United States Patent [19]

Postle

[11] 4,387,158
[45] Jun. 7, 1983

[54] PHOTOGRAPHIC MATERIALS
[75] Inventor: Stephen R. Postle, Brentwood, England
[73] Assignee: Ciba-Geigy AG, Basel, Switzerland
[21] Appl. No.: 389,728
[22] Filed: Jun. 18, 1982
[30] Foreign Application Priority Data
Jun. 19, 1981 [GB] United Kingdom ................ 8119059
[51] Int. Cl.$^3$ ............................................. G03C 1/40
[52] U.S. Cl. .................... 430/364; 430/365; 430/376; 430/402; 430/543; 430/552; 430/553; 430/565; 430/17
[58] Field of Search ............. 430/402, 543, 565, 552, 430/553, 384, 385, 549, 364, 356, 365, 376, 17
[56] References Cited

U.S. PATENT DOCUMENTS 4,126,461 11/1978 Pupo et al. ......................... 430/565
4,252,893 2/1981 Iwamuro ............................ 430/504
4,254,312 3/1981 Masuda et al. ..................... 430/381

Primary Examiner—Mary F. Downey
Attorney, Agent, or Firm—Joseph G. Kolodny

[57] ABSTRACT

Photographic silver halide material which comprises at least one silver halide emulsion layer coated on a support, there being present in the silver halide emulsion layer(s), or in a layer in operative contact with at least one silver halide emulsion layer, a compound of the formula

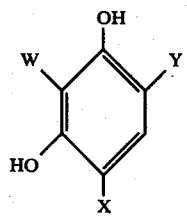

wherein W is hydrogen, alkyl, —NHCOR$^1$ or —COR$^1$, wherein R$^1$ is alkyl or alkenyl, cycloalkyl, aralkyl, aryl, phenoxymethylamino or halogen; X is a substituent in the coupling position and is a leaving group selected from hydrogen, chlorine, bromine, —SR$^{11}$ wherein R$^{11}$ is alkyl, aryl or a heterocyclic group, or X is a nitrogen-containing heterocyclic residue attached at a ring nitrogen atom; Y is a group having the formula

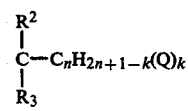

wherein Q is selected from the residues:
(a) —COOR$^4$ or —CONR$^4$R$^5$ where R$^4$ is hydrogen, alkyl optionally interrupted by 1 or more oxygen atoms, alkenyl, cycloalkyl, aralkyl or aryl, and R$^5$ is hydrogen or alkyl or R$^4$ and R$^5$, together with the nitrogen atom to which they are each bonded, may form a 5- or 6-membered heterocyclic ring;
(b) —OM wherein M is R$^5$ or —COR$^6$ wherein R$^5$ is as defined above and R$^6$ is hydrogen, alkyl, alkenyl, cycloalkyl, aralkyl or aryl;
(c) —NR$^7$R$^8$ wherein R$^7$ is hydrogen or alkyl and R$^8$ is hydrogen, or acyl or R$^7$ and R$^8$, together with the nitrogen atom to which they are bonded, form a 5- or 6-membered heterocyclic ring;
(d) —PO(OR$^9$)(O)$_x$R$^{10}$ wherein x is 0 or 1, R$^9$ is hydrogen or alkyl, R$^{10}$ is hydrogen or alkyl if x is 1, and R$^{10}$ is alkyl if x is 0 or R$^9$ and R$^{10}$ may be linked together to form an alkylene chain;
(e) —SO$_2$T where T is —OH or —NR$^4$R$^5$ wherein R$^4$ and R$^5$ are as defined above or
(f) —CN;

n is an integer from 1 to 20; k is 1 or 2; R$^2$ and R$^3$ independently are alkyl and, when Q is —CO$_2$R$^4$, either R$^2$ or R$^3$ is optionally substituted by one or two —CO$_2$R$^4$ groups, or at least one of R$^2$ and R$^3$ is so linked to the residue —C$_n$H$_{2n+1-k}$ that there is formed a cycloalkylene residue substituted by —(CO$_2$R$^4$)k in which the groups R$^4$ are the same or different and wherein R$^4$ and k are as defined above; or salts thereof with acids or bases.

The resorcinol compounds used yield good dark black image dyes when coupled in a photographic color development process.

13 Claims, 1 Drawing Figure

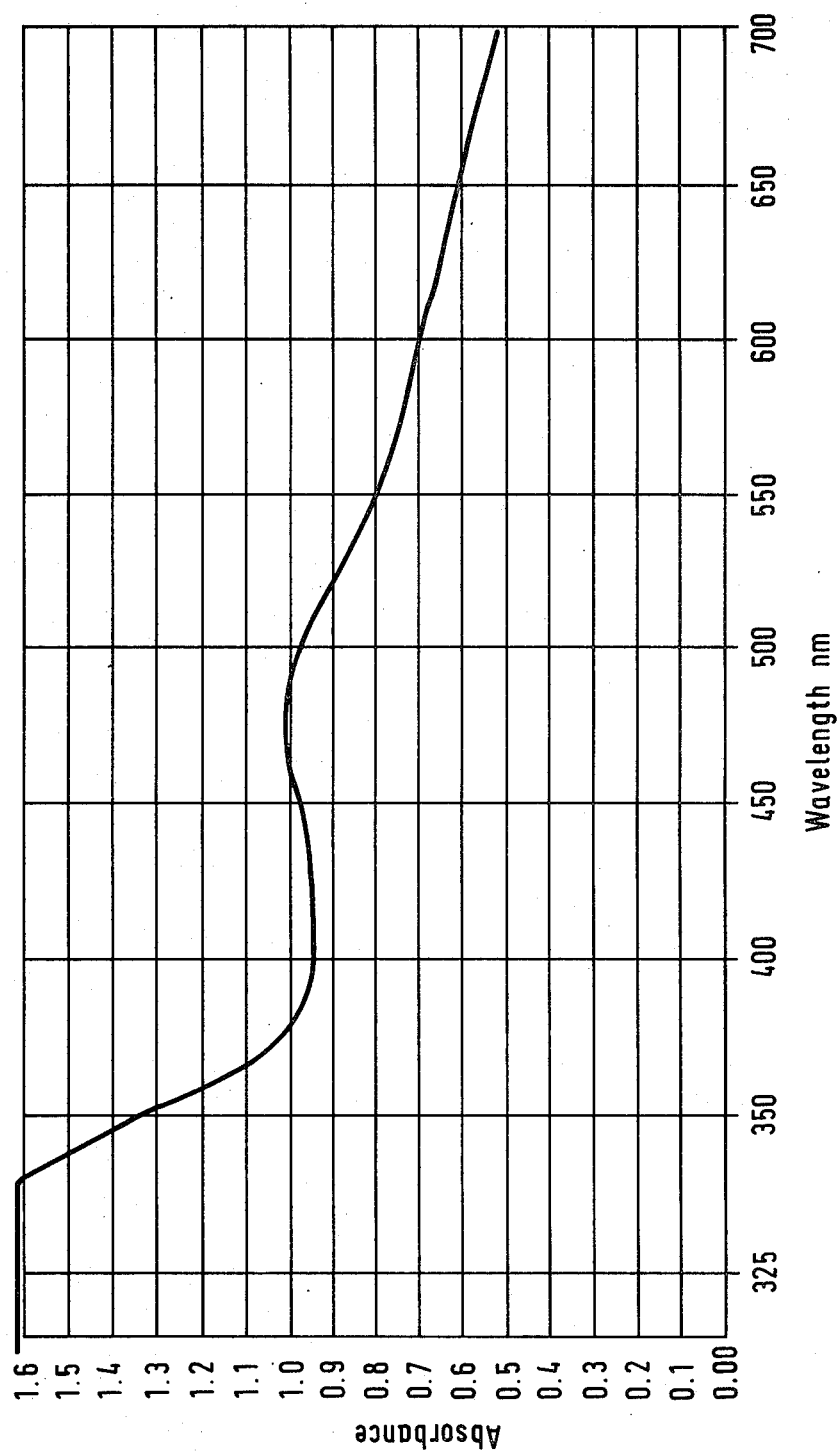

PHOTOGRAPHIC MATERIALS

This invention relates to the use of resorcinol compounds as colour couplers in photographic silver halide material.

Resorcinols containing functional substituentes directly attached to the aromatic ring are well known and are described, for instance, in Rodd's Chemistry of Carbon Compounds, 2nd Edition, Vol. III D, and in U.S. Pat. No. 4,126,461.

It has long been known that some phenolic compounds, in particular resorcinols, can be used as photographic colour couplers to yield neutral density or blackish images. However, in the past, the need to produce black images was not very great and little if any use was made of such phenolic colour couplers. Now, however, because of the very high cost of silver a great need has arisen either to replace silver as the image in silver halide sensitised photographic materials or to reinforce silver images by use of black dyes. Thus the prior art phenolic compounds have been re-examined but none of them have been found to yield black images of sufficiently good colour or density.

The subject matter of for example U.S. Pat. No. 4,126,461 relates to the use of certain resorcinol compounds as black colour couplers. However, whilst these resorcinol compounds do yield nearly acceptable black images when subjected to colour development they have been found very difficult to prepare, and the separation of non-coupling by-products therefrom has been found to be very difficult.

Two other published patent specifications which describe compounds of use as black colour couplers are GB Pat. No. 1 564 349 and published GB Application No. 2 044 474. The phenolic compounds of GB Pat. No. 1 564 349 are m-aminophenol compounds. These compounds, when colour coupled in a colour development process, yield dark blue dyes which have little density below 500 n.m. This renders them virtually useless either as a final image dye or as a negative image dye used in the production of positive prints. The compounds of GB Application No. 2 044 474 consist of two pyrazolone nuclei linked by a 4-substituted phenol. These compounds yield a visually neutral black image when colour coupled in a colour development process, but the spectrum of their colour absorption is very uneven and exhibits several peaks which renders them useless as negative images from which positive prints are printed.

We have found that a new class of compounds, namely, resorcinols substituted by a branched chain alkyl group wherein the carbon attached to the aromatic ring is a tertiary carbon atom and which bears an alkyl group containing a functional group, when used in photographic materials, overcome most of the disadvantages mentioned before. This novel class of resorcinol compounds when coupled in a photographic colour development process, yield good dark black image dyes which can be used as the final dye image either alone or with a silver image in a positive print or which can be used to form a negative image from which a positive print may be obtained.

Thus according to the present invention there is described a photographic silver halide material which comprises at least one silver halide emulsion layer coated on a support, there being present in the silver halide emulsion layer(s), or in a layer in operative contact with at least one silver halide emulsion layer, a compound of the formula

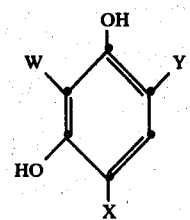 (1)

wherein
W is hydrogen, n-alkyl having 1 to 5 carbon atoms, —NHCOR$^1$ or —COR$^1$ wherein R$^1$ is alkyl having 1 to 12 carbon atoms or alkenyl having 2 to 12 carbon atoms, cycloalkyl having 3 to 8 carbon atoms, aralkyl having 7 to 13 carbon atoms or aryl having 6 to 10 carbon atoms optionally substituted by one or two alkyl groups each having 1 to 4 carbon atoms, a phenoxymethylamino group optionally substituted with one or more alkyl groups, or halogen;

X is hydrogen, chlorine, bromine, a group of formula —SR$^{11}$ wherein R$^{11}$ is alkyl having 1 to 20 carbon atoms, aryl having 6 to 10 carbon atoms optionally substituted by one or two alkyl groups each having 1 to 4 carbon atoms, or a heterocyclic group, or X is a nitrogen-containing heterocyclic residue attached at a ring nitrogen atom;

Y is a group having the formula

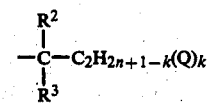 (2)

wherein Q is selected from the residues:

(a) —COOR$^4$ or —CONR$^4$R$^5$, where R$^4$ is hydrogen, alkyl having 1 to 20 carbon atoms optionally interrupted by 1 or more oxygen atoms, alkenyl having 3 to 20 carbon atoms, cycloalkyl having 3 to 12 carbon atoms, aralkyl having 7 to 13 carbon atoms or optionally substituted aryl having 6 to 10 carbon atoms and R$^5$ is hydrogen or alkyl having 1 to 20 carbon atoms or R$^4$ and R$^5$, together with the nitrogen atom to which they are each bonded, form a 5- or 6-membered heterocyclic ring optionally substituted by alkyl having 1 to 4 carbon atoms, (b) —OM wherein M is R$^5$ or —COR$^6$ wherein R$^5$ is as defined above and R$^6$ is hydrogen, alkyl having 1 to 20 carbon atoms, alkenyl having 3 to 20 carbon atoms, cycloalkyl having 3 to 12 carbon atoms, aralkyl having 7 to 13 carbon atoms or optionally substituted aryl having 6 to 10 carbon atoms, (c) —NR$^7$R$^8$ wherein R$^7$ is hydrogen or alkyl having 1 to 4 carbon atoms and R$^8$ is hydrogen, alkyl having 1 to 4 carbon atoms or acyl of the formula —COR$^4$ wherein R$^4$ is as defined above or R$^7$ and R$^8$, together with the nitrogen atom to which they are bonded, form a 5- or 6-membered heterocyclic ring optionally substituted by alkyl having 1 1 to 4 carbon atoms, (d) —P(O)(OR$^9$)(O)$_x$R$^{10}$ wherein x is 0 or 1, R$^9$ is hydrogen or alkyl having 1 to 20 carbon atoms, R$^{10}$ is hydrogen or alkyl having 1 to 20 carbon atoms if x is 1, and R$^{10}$ is alkyl containing 1 to 5 carbon atoms if x is 0 or R$^9$ and R$^{10}$ may be linked together to form an alkylene chain having 2 or 3 carbon atoms optionally substituted by one or more alkyl groups each having 1 to 20 carbon atoms, (e) —$SO_2T$ where T is —OH or —$NR^4R^5$ wherein $R^4$ and $R^5$ are as defined above and (f) —CN, n is an integer from 1 to 20; k is 1 or 2; $R^2$ and $R^3$ independently are alkyl having 1 to 5 carbon atoms, and, if Q is —$CO_2R^4$, either $R^2$ or $R^3$ is optionally substituted by one or two —$CO_2R^4$ groups, or at least one of $R^2$ and $R^3$ is so linked to the residue —$C_nH_{2n+1-k}$— that there is formed a cycloalkylene residue having 5 to 12 carbon atoms substituted by —$(CO_2R^4)_k$ in which the groups $R^4$ are the same or different and wherein $R^4$ and k are as defined above, or salts thereof with acids or bases.

According to a further aspect of the present invention there is provided a process for the production of a photographic black dye image which comprises imagewise exposing photographic material of the present invention as just defined, colour developing the exposed material using a colour developing solution which comprises an aqueous alkaline solution of a primary aromatic amine colour developing agent to form simultaneously a silver image and a black dye image, optionally bleaching the silver image, and then fixing out all the silver halide in the material using an aqueous solution of a silver halide solvent.

The substituent W in the compounds of the formula (1) is hydrogen or alkyl. Preferred alkyl radicals are n-alkyl radicals and preferably those having 1 to 5 carbon atoms such as methyl, ethyl, propyl, butyl, or pentyl. W denotes further acylamino of the formula —NH-$COR^1$ wherein $R^1$ is alkyl having 1 to 12 carbon atoms such methyl, ethyl, propyl, butyl, pentyl, hexyl, heptyl, octyl, nonyl, decyl and dodecyl as well as isomers thereof. Preferred are those alkyl radicals $R^1$ containing 1 to 6 carbon atoms. $R^1$ further denotes alkenyl. These radicals are derivable from the corresponding alkyl groups listed for $R^1$. Preferred alkenyl radicals are those having 2 to 16 carbon atoms such as vinyl, prop-1-enyl, 1-methylvinyl, but-1-enyl, hexa-2,4-dienyl, undec-10-enyl and dodec-1-enyl. $R^1$ denotes further cycloalkyl. Suitable cycloalkyl radicals contain 3 to 8 carbon atoms such as cyclopropyl, cyclopentyl, cyclohexyl and cyclooctyl. Preferred is cyclohexyl. $R^1$ denotes further aralkyl.

Preferred aralkyl radicals contain 7 to 13 carbon atoms such as benzyl, phenethyl, benzhydryl, and naphthylmethyl. Benzyl is mostly preferred. In the meaning of aryl, $R^1$ represent a ring system having 6 to 10 carbon atoms such as phenyl and naphthyl. These aryl rings as well as the aryl nucleus of the said aralkyl radicals $R^1$ are optionally substituted by one or two alkyl groups. Preferably, these alkyl substituents contain 1 to 4 carbon atoms. Methyl and ethyl are mostly preferred. W denotes further acyl. Preferred acyl groups have the formula —$COR^1$ wherein $R^1$ has exactly the same meaning as in the group —$NHCOR^1$, —$COCH_3$ and —$COC_6H_5$ are especially preferred. Further, W is a phenoxymethylamino group which is optionally substituted with one or more alkyl groups. Preferably these alkyl groups contain 1 to 10 carbon atoms. Mostly preferred are methyl, t-butyl, t-pentyl and t-octyl. Preferably, 1 or 2 of these alkyl groups are substituents on the phenyl ring of the phenoxymethyl amino group. W denotes further halogen. Suitable halogen radicals are fluorine and especially chlorine and bromine.

X is hydrogen, halogen such as chlorine and bromine or a mercapto group of the formula —$SR^{11}$. $R^{11}$ is alkyl preferably having 1 to 20 carbon atoms. In addition to those alkyl radicals listed above for $R^1$, preferably the radicals tetradecyl, pentadecyl, hexadecyl, octadecyl, eicosyl and their isomers are operable as $R^{11}$ in the group —$SR^{11}$. $R^{11}$ is further aryl, preferably having 6 to 10 carbon atoms such as phenyl and naphthyl which rings are optionally substituted by 1 or 2 alkyl groups (each) having 1 to 4 carbon atoms. In the meaning of a heterocyclic group, $R^{11}$ denotes preferably a 3 to 7 membered ring, containing one or more oxygen, nitrogen or sulphur atoms it may be for example, oxirane, azetidine, furan, thiophene, pyrrole, oxazole, isocazole, thiazole, isothiazole, pyrazole, imidazole, triazole, oxadiazole, thiadiazole, thiatriazole, tetrazole, pyridine, pyrimidine, pyrazine, pyridazine, triazine or azepine. X is further a nitrogen-containing heterocyclic residue attached at the resorcinol nucleus by a ring nitrogen atom. Preferred heterocyclic rings X are 5 to 7 membered rings containing one or more nitrogen atoms, and optionally an oxygen or sulphur atom, it may be, for example, pyrrolidin-dione or piperidin-dione.

Y is a group of the formula

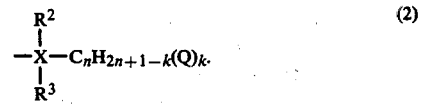

(2)

In these radicals Q denotes a group of the formula —$COOR^4$ or —$CONR^4R^5$.

$R^4$ is hydrogen or alkyl, preferably containing 1 to 20 carbon atoms. Suitable alkyl radicals $R^4$ are those listed in the definitions of $R^1$ and $R^{11}$. Preferred are the alkyl radicals having 1 to 12 carbon atoms. The alkyl groups $R^4$ are optionally interrupted by 1 or more, particularly 2 oxygen atoms. Further, $R^4$ is alkenyl having 3 to 20 carbon atoms. Suitable alkenyl radicals are those listed above for $R^1$. Preferred are for example, prop-2-enyl, but-2-enyl, 3-methyl-but-2-enyl, octadec-9-enyl and eicos-2-enyl. $R^4$ denotes further cycloalkyl, preferably containing 3 to 12 carbon atoms such as cyclopropyl, cyclobutyl, cyclopentyl, cyclohexyl, cyclooctyl and cyclodecyl, cyclododecyl as well as cycloalkyl systems which are bi- or tri-cyclic such as adamantyl e.g. $R^4$ denotes further aralkyl. Preferred aralkyl radicals contain 7 to 13 carbon atoms such as benzyl, phenethyl, benzhydryl and naphthaylmethyl. Preferred aryl groups $R^4$ contain 6 to 10 carbon atoms are e.g. phenyl and naphthyl which are optionally substituted by one or two alkyl groups each having 1 to 4 carbon atoms, or by one or two —$CF_3$, —CN, —$CONH_2$, —$COOCH_3$, —$NO_2$, —$OCH_3$ or halogen groups. $R^5$ is hydrogen or alkyl preferably having 1 to 20 carbon atoms, more preferably 1 to 10 and most preferably 5 to 10 carbon atoms. $R^4$ and $R^5$, together with the nitrogen atom to which they are bonded, form a heterocyclic ring. Preferred are 5- to 6-membered heterocyclic rings such as morpholinyl or piperidinyl radicals which are optionally substituted by alkyl, preferably containing 1 to 4 carbon atoms.

Further, Q denotes a radical of the formula —OM, wherein M is $R_5$ as just defined above or an acyl group such as —$COR^6$. $R^6$ is hydrogen or alkyl having 1 to 20 carbon atoms. Suitable alkyl radicals are those listed above in the definition of $R^{11}$. Preferably, these alkyl radicals contain 1 to 10 or, more preferably, 1 to 5 carbon atoms. $R^6$ is further alkenyl, preferably having 3 to 20 carbon atoms. Suitable alkenyl radicals which preferably contain 3 to 10 carbon atoms are derivable from the alkyl radicals $R^6$. Further, $R^6$ denotes cycloalkyl preferably containing 3 to 12 carbon atoms. Suitable radicals are listed above for $R^4$. In the meaning of aralkyl, $R^6$ contains preferably 7 to 13 carbon atoms and is e.g. benzyl, phenethyl, benzhydryl, and naphthylmethyl. $R^6$ denotes further aryl, preferably containing 6 to 10 carbon atoms such as phenyl or naphthyl, e.g., which aryl radicals are optionally substituted by alkyl having 1 to 10, preferably 5 to 10 carbon atoms. Most preferably, these alkyl radicals are branched radicals.

Further, Q denotes an amino group. Suitable amino groups correspond to the formula $-NR^7R^8$. $R^7$ is this formula is hydrogen or alkyl such as methyl, ethyl, propyl, i-propyl and butyl. $R^8$ is hydrogen, further alkyl such as methyl, ethyl, propyl, isopropyl and butyl, and further an acyl group of the formula $-COR^4$ wherein $R^4$ is as defined above. $R^7$ and $R^8$ form together with the nitrogen atom to which they are bonded a heterocyclic ring. Preferably, this ring is 5- or 6-membered and in e.g. a pyrrolidinyl, piperidinyl or morpholine ring.

The heterocyclic rings are optionally substituted by alkyl having 1 to 4 carbon atoms.

Q denotes further a group of the formula $-P(O)(OR^9)(O)_xR^{10}$ wherein x is 0 or 1. $R^9$ is hydrogen or alkyl having 1 to 20 carbon atoms. Suitable alkyl groups are listed above in the definition of $R^6$. Preferred alkyl groups contain 1 to 10 or, more preferably, 1 to 5 carbon atoms. The index x is 0 or 1. $R^{10}$ has the same meaning as $R^9$ if x is 1; and $R^{10}$ is alkyl containing 1 to 5 carbon atoms such as methyl, ethyl, propyl, i-propyl, butyl, pentyl or i-pentyl if x is 0.

$R^9$ and $R^{10}$ are further linked together to form an alkylene chain. Preferably, this alkylene chain contains 2 or 3 carbon atoms which are optionally substituted by one or more, preferably one or two, alkyl groups each having 1 to 20 carbon atoms. Suitable alkyl groups are listed above in the definition of $R^6$.

Q further denotes a group of the formula $-SO_2T$, where T is hydroxy or an amino group of the formula $-NR^4R^5$. $R^4$ and $R^5$ are as defined above. Preferably $R^4$ and $R^5$ have the same meaning and are alkyl having 1 to 5 carbon atoms such as methyl, ethyl, propyl, i-propyl, butyl, pentyl or i-pentyl.

Q further denotes cyano.

n is an integer from 1 to 20, or, preferably from 1 to 10, k is 1 or 2.

$R^2$ and $R^3$ independently are alkyl preferably having 1 to 5 carbon atoms such as methyl, ethyl, n-propyl, iso-propyl, n-butyl, s-butyl, n-pentyl, or neopentyl. If Q denotes $-CO_2R^4$, either $R^2$ or $R^3$ is optionally substituted by one or two $-CO_2R^4$ groups or at least one of $R^2$ and $R^3$ is so linked to the residue $-C_nH_{2n+1-k}$ that there is formed a cycloalkylene residue preferably containing 5 to 12 carbon atoms, more preferably a cyclohexylene ring, substituted by $-(CO_2R^4)_k$ wherein $R^4$ are the same or different and wherein $R^4$ and k are as defined above. When the groups $R^9$ and $R^{10}$ are linked to form said methylene chain optionally substituted by one or more $C_1$ to $C_{20}$ alkyl groups they may be for example, $-CH_2CH_2-$, $-CH_2CH_2CH_2-$, $-CH_2CH(CH_3)-$, $-CH_2CH(C_2H_5)-$, $-CH_2CH(C_{20}H_{41})-$, $-CH(CH_3)CH(CH_3)-$, $-CH(CH_3)C(CH_3)_2-$, $-C(CH_3)_2C(CH_3)_2-$, $-CH_2CH_2C(CH_3)_2-$ or $-CH(CH_3)CH_2CH(CH_3)-$.

Examples of salts of the compounds of the formula (1) are those formed from the alkali metals, the alkaline earth metals, transition element cations and ammonium and substituted ammonium cations. Examples of salts of the compounds of the formula (1) which contain a residue Q wherein Q is $-NR^7R^8$ are the hydrochloride, sulphate, p-toluene sulphonate, maleate and oxalate salts.

When k in formula (2) is 2 and Q is a residue of group (a), the two groups Q may be the same or different; likewise, when $R^2$ or $R^3$ is substituted by $-CO_2R^4$, $R^4$ therein may be the same as or different from the group $R^4$ in the residue Q.

Preferably, the material contains a resorcinol compound of the formula (1) wherein W is hydrogen, n-alkyl having 1 to 5 carbon atoms, cyclopentyl, cyclohexyl, phenyl optionally substituted by one or two alkyl groups each having 1 to 4 carbon atoms or W is halogen, X is hydrogen, chlorine, bromine, $-SR^{11}$ where $R^{11}$ is alkyl having 1 to 10 carbon atoms, phenyl optionally substituted by one or two alkyl groups each having 1 to 4 carbon atoms or a tetrazolyl ring optionally substituted by alkyl having 1 to 4 carbon atoms or phenyl, Y is a group of the formula

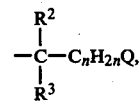

where Q is $-COOR^4$ or $-CONR^4R^5$ where $R^4$ is hydrogen, alkyl having 1 to 12 carbon atoms optionally interrupted by 1 or 2 oxygen atoms, benzyl or phenyl and $R^5$ is hydrogen or alkyl having 1 to 10 carbon atoms, or $R^4$ and $R^5$, together with the nitrogen atom to which they are bonded form a morpholinyl or a piperidinyl radical, or Q is $-OM$, where M is hydrogen or alkyl having 1 to 5 carbon atoms, or M is $-COR^6$ where $R^6$ is hydrogen, alkyl having 1 to 10 carbon atoms, cyclohexyl, phenyl or benzyl, or Q is $-NR^7R^8$ where $R^7$ is hydrogen or alkyl having 1 to 4 carbon atoms and $R^8$ is $-COR_4$ where $R_4$ is as defined above, or Q is $-P(O)(OR^9)_2$ where $R^9$ is alkyl having 1 to 10 carbon atoms, or Q is $-SO_2T$ where T is hydroxy or $-NR^4R^5$ where $R^4$ and $R^5$ are as defined above, $R^2$ and $R^3$ are alkyl having 1 to 5 carbon atoms or at least one of $R^2$ and $R^3$ is so linked to the residue $-C_nH_{2n}-$ that there is formed a cycloalkyl group having 5 to 8 carbon atoms optionally substituted by a group $-COOR^4$ where $R^4$ is as defined above, and n is an integer from 1 to 20.

Further preferred material contains a resorcinol compound of the formula (1) wherein W is hydrogen, methyl, chlorine or bromine, X is hydrogen, chlorine, bromine or a group of the formula

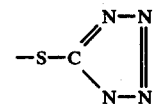

and Y is a group of the formula

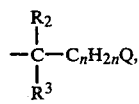

wherein Q is —COOR⁴ or —CONR⁴R⁵, where R⁴ is hydrogen or alkyl having 1 to 12 carbon atoms and R⁵ is alkyl having 5 to 10 carbon atoms or phenyl optionally substituted by alkyl having 1 to 4 carbon atoms, or Q is —OM, where M is hydrogen or —COR₆ where R₆ is alkyl having 1 to 5 carbon atoms, or Q is —NHR₈ where R₈ is —COR₆ where R₆ is as just defined or Q is —P(O)(OR₉)₂, where R₉ is alkyl having 1 to 5 carbon atoms, or Q is —SO₂NR⁶R⁶ where R⁶ is as defined above, and R₂ and R₃ are alkyl having 1 to 5 carbon atoms or R₂ forms together with the residue —C$_n$H$_{2n}$— a cyclohexyl group substituted by —COOR⁴ where R⁴ is as defined above, and n is an integer from 1 to 10.

Especially preferred are those compounds of the formula (1), wherein R² is methyl. In further suitable compounds of the formula (1), substituent W is hydrogen, methyl, ethyl, butyl, —NHCOR¹ wherein R¹ is alkyl having 1 to 6 carbon atoms or alkenyl having 2 to 6 carbon atoms, cyclohexyl, benzyl, phenyl optionally substituted by one or two methyl or ethyl groups, or W is chlorine or bromine. Preferably, W is hydrogen, methyl, —NHCOCH₂C₆H₅, a phenoxymethylamino group optionally substituted with one or more alkyl groups, chlorine or bromine.

Preferably, in compounds of the formula (1), n is 1 to 10, k is 1, R³ is alkyl having 1 to 5 carbon atoms, Q is —CO₂R⁴ or —CONR⁴R⁵, —NR⁷R⁸ or —OM wherein R⁴, R⁵, R⁷, R⁸ and M are as defined above and W is hydrogen, methyl, —NHCOCH₂C₆H₅, —NHCOC₆H₅ or a phenoxymethylamino group optionally substituted with one or more alkyl groups, chlorine or bromine.

Preferred compounds of the formula (1) are those wherein n is 3 to 5, k is 1, R³ is methyl, Q is —CO₂R⁴ or —CONR⁴R⁵ or —NR⁷R⁸ wherein R⁴, R⁵, R⁷ and R⁸ are as defined above, and W is hydrogen, methyl, —NHCOCH₂C₆H₅, —NHCOC₆H₅ or a phenoxymethylamino group optionally substituted with one or more alkyl groups.

It is to be understood that the substituents W and Y can influence the spectral absorption of the black dye of the coupled resorcinol compounds of the formula (1). However, the substituent X cannot influence the spectral absorption of the dye as this substituent leaves during the coupling reaction. However, the substituent can affect the coupling rate and sometimes increased coupling activity is obtained when X is either a chlorine or bromine atom rather than a hydrogen atom. The group —SR¹¹ may be a so-called development inhibiting group and sometimes it is preferred to include a D.I.R. resorcinol coupler of this type in the photographic material to cause inter- and intra-image effects such as image edge-enhancement.

The inventively used compounds of the formula (1) are prepared by reacting in the presence of an acid or Friedel-Crafts catalyst and in the temperature range 20° to 150° C., a compound having the formula

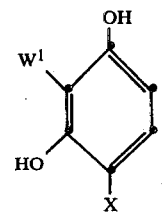

wherein X is as defined above, W¹ is hydrogen, n-alkyl having 1 to 5 carbon atoms, —NH₂, —NHCOR¹ or —COR¹ wherein R¹ is as defined above, —NO₂ or halogen with a functional alkylating agent capable of introducing a group of the formula

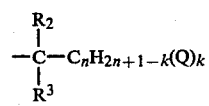

wherein R², R³, Q, n and k are as defined above, optionally reducing any nitro group W¹ to an amino group, and then acylating this amino group to form a group —NHCOR¹ wherein R¹ is as defined above; and optionally introducing into the 2- or 6-position substituents W and/or X which are respectively other than hydrogen.

The reactants of formula (3) are well-known and can be produced by methods well known per se.

The ratio of the aromatic phenol (3) to alkylating species is between 10:1 and is preferably between 5:1 and 1:1. The excess of the phenol (3) may act as a solvent.

In a further process for the preparation of the inventively used resorcinols, the introduction of the group —NHCOR¹ at the 2-position of the ring, is accomplished in the following manner:

A compound of the formula

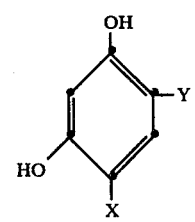

wherein X and Y are as defined above, is nitrated with nitric acid, or other nitrating agent known to those skilled in the art of nitrating phenolic compounds, to give a compound of the formula

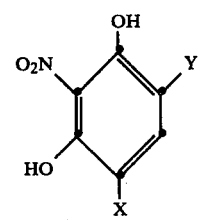

wherein X and Y are as defined above which compound may then be reduced, using catalytic hydrogenation or other reduction process known to those skilled in the art, to give a compound of the formula

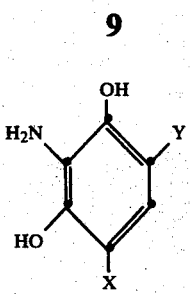

(5)

wherein Y and X are as defined above which compound may then be N-acylated with an acylating species capable of introducing the residue $R^1CO-$, for example an ester, acid halide, acid azide, acid anhydride, for example, a mixed anhydride of the acid $R^1COOH$ formed with a mono-esterified carbonic acid, pivalic acid or trichloroacetic acid, or with the free itself in the presence of a condensing agent, for example, a carbodiimide, to give a compound of the formula

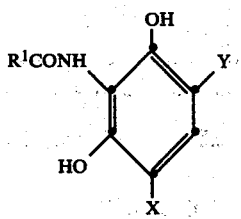

(1c)

wherein $R^1$, X and Y are as defined above. Compounds of the formula (4) and (5) suitable for reduction and/or acylation may also be obtained from compounds of the formula (3) as hereinbefore described.

In a further process for the preparation of the inventively used resorcinols, halogen, interhalogen or $R^{11}S-$ groups may be introduced into a compound of the formula

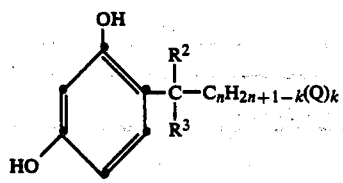

(6)

by reaction of the compounds of formula (6) with up to three mols of a halogen, interhalogen or $R^{11}-S-$ compound of the formula $W^2-Cl$, or $W^2-Br$, wherein $W^2$ may be chlorine, bromine or $R^{11}S-$, to give a compound of the formula

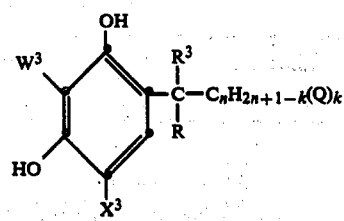

(1d)

wherein $W^3$ and $X^3$ are, independently, $W^2$ or hydrogen, providing that both $W^3$ and $X^3$ are not both hydrogen, and $R^2$, $R^3$, n, Q and k are as defined above.

Preferably the compound of the formula (1) is present in the silver halide emulsion layer.

The photographic material of the present invention which comprises in a layer thereof a compound of the formula (1) is processed after exposure by a colour development process using a primary aromatic amine colour developing agent of know type. As usual in colour development processes the primary aromatic amine developing agent reduces the latent silver image to form a silver image and becomes oxidised, and the oxidised colour developer couples with the resorcinol couplers of the formula (1) to form a black dye image in conformity with the black silver image. Resorcinol compounds which are either unsubstituted or have a leaving group in the 6-position that is to say ortho to one $-OH$ group are known to couple with the oxidation products or oxidised colour developer and this 6-position is known as the coupling position. In some instances the density of the black dye is sufficient to form the final image in the material and in such a case the developed silver is bleached and the silver halide is fixed out to recover all the silver. In other cases it is preferred to use the black dye image to reinforce the silver image and so reduce the silver content in the original material.

Thus by layer in operative contact with a layer which contains silver halide is meant a layer which is close enough to the layer which contains the silver halide for oxidised colour developer to diffuse imagewise to this layer to couple with the compound of the formula (1) to form a black dye image in conformity with the silver image in the silver halide layer.

Where a silver bleach step is employed this may be combined with the fixing step by employing a bleach-fix (blix)bath.

Suitable primary aromatic amine colour developing agents are p-phenylenediamine compounds, for example 4-amino-N,N-dimethylaniline hydrochloride, 4-amino-N,N-diethylaniline hydrochloride, 4-amino-3-methyl-N,N-diethylaniline hydrochloride and p-aminophenol compounds for example a p-aminophenol itself and 2,6-dichloro-4-aminophenol.

The compounds of the formula (1) are preferably incorporated into the photographic material and most preferably into the silver halide emulsion layer in an oil dispersion.

The amounts of the compound of the formula (1) present in the photographic material depend on whether the photographic material which incorporates the compound is designed to be processed so that the silver image remains or is removed to leave only the black dye image.

A suitable amount of the compound of the formula (1) to be present in a negative film material in which no silver image is left is 50–100 mg/dm² and in which the silver image is retained is 25–50 mg/dm².

Suitable amounts of the compound of the formula (1) to be present in positive print material in which no silver is left are 20–40 mg/dm² and in which the silver image is retained are 10–20 mg/dm².

When the photographic material of the present invention is employed as a camera negative film there is sometimes one silver halide emulsion layer which comprises a compound of the formula (1) or two silver halide emulsion layers each of which comprises a compound of the formula (1). Suitable silver coating weights of such silver halide emulsion layers are 50–100 mg/dm².

When the photographic material is to be used as camera negative film material, the material is most usually processed to leave no silver image present, only the black dye image.

When the photographic film material of the present invention is to be used as a positive print material most preferably the silver image is left so that the black dye enhances the silver image but does not wholly replace it. Preferably such material comprises one silver halide emulsion layer which contains a compound of the formula (1). Suitable silver coating weights for such silver halide emulsion layers are 2–15 mg/dm$^2$.

When the photographic material of the present invention is to be used as an X-ray film there is usually one silver halide emulsion layer coated on each side of the transparent film base and present in each silver halide emulsion layers is a compound of the formula (1). Usually such X-ray film material is processes to leave the silver image so that the black dye image reinforces the silver image.

Suitable silver halide coating weights of such silver halide emulsion layers are 50–100 mg/dm$^2$.

Any of the silver halides used in photographic materials can be used in the photographic material of the present invention, for example silver chlorobromide, silver chloride, silver iodobromide, silver bromide and silver iodobromochloride.

The silver halide crystals may be chemically sensitised by any of the well known means, for example by use of sulphur, selenium and noble metals. Examples of suitable sensitising compounds are sodium thiosulphate and mercury, gold, palladium and platinum salts.

The emulsions used in the photographic material of the present invention may be optically sensitised by the addition of optical sensitisers, for example carbocyanine and merocyanine dyes, to the emulsions.

These emulsions may contain any of the additives commonly used in photographic emulsions, for example wetting agents, stabilising agents, polyethylene oxides, metal sequestering agents and growth or crystal habit modifying agents commonly used for silver halide such as adenine.

Preferably the dispersing medium is gelatin or a mixture of gelatin and a water-soluble latex, for example a latex vinyl acrylate-containing polymer. Most preferably if such a latex is present in the final emulsion it is added after all crystal growth has occurred. However other water-soluble colloids, for example casein, polyvinyl-pyrrolidine or polyvinyl alcohol, may be used alone or together with gelatin.

The support used in the photographic material of the present invention may be any one of the supports commonly used for photographic materials, for example baryta coated paper base, polyethylene laminated paper base, cellulose triacetate, cellulose acetate butyrate and subbed and axially oriented polyethylene terephthalate.

The following Examples further illustrate the present invention. Parts and percentages shown therein are by weight. Pressures are given in millibars. Examples 1 to 13 relate to the preparation of compounds of formula (1).

EXAMPLE 1

110 Parts of resorcinol, 28.4 parts of methyl 5-methylhex-5-enoate (prepared in accordance with U.S. Pat. No. 3,783,136) and 5.0 parts of the active earth Fulmont 23 (trademark) are stirred at 125°–130° C. for 18 hours. The cooled reaction mixture is diluted with ether, filtered free of catalyst, and the ether stripped off.

The residual oil is then distilled to give 91.0 parts of a fraction boiling up to 190° C. at a pressure of 10 mm of mercury (b.p. (10)) consisting mainly of resorcinol followed by 30 parts of a fraction b.p. (0.2) 186°–194° C. This fraction, after dilution with petroleum ether (b.p. 40°–60° C.) containing a little ether, yields methyl-5-(2,4-dihydroxyphenyl)-5-methylhexanonate of the formula

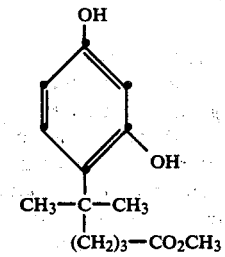

m.p. 93°–96° C., with the following percentage composition by weight:

|  | Carbon | Hydrogen |
| --- | --- | --- |
| Found | 66.34 | 8.13 |
| Calculated for C$_{14}$H$_{20}$O$_4$ | 66.65 | 7.99 |

EXAMPLE 2

In the manner described in Example 1, 55 parts of resorcinol, 15.4 parts of 4-carbomethyl-1-methylcyclohex-1-ene (prepared in accordance with Kojima et al., J. Org. Chem. 36, 924 (1971)) and 5.0 parts of Fulmont 237 (trademark) are reacted and worked up. Distillation yields 42.6 parts of recovered resorcinol followed by 15.4 parts of cis and trans-4-carbomethoxy-1-(2,4-dihydroxyphenyl)-1-methylcyclohexane b.p. (0.3) 218° C. with the following percentage composition by weight:

|  | Carbon | Hydrogen |
| --- | --- | --- |
| Found | 67.93 | 7.77 |
| Calculated for C$_{15}$H$_{20}$O$_4$ | 68.16 | 7.63 |

EXAMPLE 3

7-(2,4-Dihydroxyphenyl)-3,7-dimethyloctan-1-ol, 36 parts, b.p. (0.2) 210° C. are obtained from 73 parts of resorcinol, 52 parts citronellol, and 60 parts of Fulmont 237 (trademark) following the procedure of Example 1, and has the following percentage composition by weight.

|  | Carbon | Hydrogen |
| --- | --- | --- |
| Found | 72.56 | 10.40 |
| Calculated for C$_{16}$H$_{26}$O$_3$ | 72.14 | 9.84 |

EXAMPLE 4

11.0 Parts of resorcinol, 10.0 parts of citronellyl acetate and 0.5 parts of p-toluene sulphonic acid are heated at 115° C. for 45 hours. The reaction mixture is then taken up in ether, washed with sodium bicarbonate solution, water, and evaporated. The residual oil is distilled and yields 3.9 parts of 7-(2,4-dihydroxyphenyl)-

3,7-dimethyloct-1-yl acetate b.p. (0.2) 215° C. with the following percentage composition by weight:

|  | Carbon | Hydrogen |
|---|---|---|
| Found | 70.44 | 9.20 |
| Calculated for $C_{18}H_{28}O_4$ | 70.09 | 9.15 |

EXAMPLE 5

(a) To 36.3 parts of 2-amino-6-hydroxy-6-methylheptane (prepared according to J. Doeuvre and J. Poizat. Compt. rend. 224, 286–8 (1947)) in 100 parts of ether, is added 25.5 parts of acetic anhydride, with stirring, while keeping the temmperature at 20° C.

On completion of the addition, the reaction mixture is stirred for a further 30 minutes and the volatiles removed under reduced pressure. Distillation of the residual oil yields 35.4 parts of 2-acetamido-6-hydroxy-6-methylheptane b.p.(12) 196°–198° C. with the following percentage composition by weight:

|  | Carbon | Hydrogen | Nitrogen |
|---|---|---|---|
| Found | 63.90 | 11.71 | 7.66 |
| Calculated for $C_{10}H_{21}NO_2$ | 64.13 | 11.30 | 7.48 |

(b) 11.0 Parts of resorcinol, 7.5 parts of 2-acetamido-6-hydroxy-6-methylheptane and 0.5 parts of p-toluene sulphonic acid are sealed for 3 days at 120° C. in a glass Carius tube.

The reaction mixture, after dilution with ether, is washed with sodium bicarbonate solution, then water and evaporated. Distillation of the residual oil after a fore-run of 5.1 parts of resorcinol, yields 6.3 parts of 2-acetamido-6-(2,4-dihydroxyphenyl)-6-methylheptane b.p.(0.2) 234°–240° C. This fraction, after dilution with ether, crystallised to give a white solid m.p. 197°–200° C. with the following percentage composition by weight:

|  | Carbon | Hydrogen | Nitrogen |
|---|---|---|---|
| Found | 68.59 | 9.03 | 4.95 |
| Calculated for $C_{16}H_{25}NO_3$ | 68.79 | 9.02 | 5.01 |

EXAMPLE 6

0.64 parts of 5-mercapto-1-methyltetrazole are suspended in 17 parts of 1,1,1-trichloroethane and chlorine bubbled through this mixture until complete dissolution is obtained. The whole is evaporated to dryness under reduced pressure, treated twice with further portions of trichloroethane and evaporated to dryness. The residue is taken up in 19 parts of trichloroethane and added dropwise, under nitrogen and with protection from moisture, over 15 minutes to a refluxing solution of 1.26 parts of methyl-5-(2,4-dihydroxyphenyl)-5-methylhexanoate according to Example 1 in 19 parts of trichloroethane. The mixture is held at reflux for 8 hours, then cooled, filtered free of a small amount of solid and evaporated to dryness to give a non-volatile oil which is purified by preparative layer chromatography (silica/1:1 ethyl acetate/cyclohexane) to give as a glass methyl-5-[2,4-dihydroxy-5-(1-methyltetrazol-5-yl-thio)-phenyl]-5-methylhexanoate of the formula

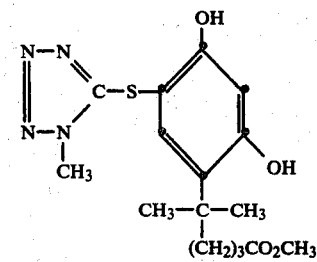

EXAMPLE 7

5.5 parts of methyl-5-(2,4-dihydroxyphenyl)-5-methylhexanoate, 50 parts of n-hexanol, and 0.5 parts of p-toluene sulphonic acid are heated on a steam-bath for 6 hours. The excess hexanol is then removed under reduced pressure and then residual oil taken up in ether, washed with sodium bicarbonate solution, water, and evaporated. Short path distillation of the residual oil at a pressure of 0.5 mm of mercury yields 5.8 parts of n-hexyl-5-(2,4-dihydroxyphenyl)-5-methylhexanoate of the formula

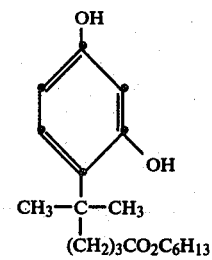

with the following percentage composition by weight:

|  | Carbon | Hydrogen |
|---|---|---|
| Found | 70.69 | 9.71 |
| Calculated for $C_{19}H_{30}O_4$ | 70.77 | 9.38 |

EXAMPLE 8

10.0 Parts of 2-methylresorcinol, 5.7 parts of 5-methylhex-5-enoate and 2.5 parts of Fulmont 327 (trademark) are reacted together, and worked up, as described in Example 1. Distillation yields methyl 5-(2,4-dihydroxy-3-methylphenyl)-5-methyl-hexanoate b.p. (0.7) 196° C. having the following percentage composition by weight.

|  | Carbon | Hydrogen |
|---|---|---|
| Found | 67.95 | 8.57 |
| Calculated for $C_{15}H_{22}O_4$ | 67.65 | 8.33 |

EXAMPLE 9

11.0 parts of resorcinol, 12.2 parts of 2-hexanoylamino-6-hydroxy-6-methyl-heptane and 0.5 parts of p-toluene sulphonic acid are sealed for 4 days in a glass Carius tube. The reaction mixture is then poured into 500 parts of water and stirred for 30 minutes on a steam-bath. After removing the water by decantation, the above washing procedure is repeated twice again before taking up the residual oil in ether. The ether solution is then dried and stripped down under reduced pressure (16 mb) on a rotary evaporator at 100° C. to give 2-hexanoylamino-6-(2,4-dihydroxphenyl)-6-methylheptane as an amber oil with the following percentage composition by weight.

|  | Carbon | Hydrogen | Nitrogen |
|---|---|---|---|
| Found | 71.19 | 10.29 | 4.02 |
| Calculated for $C_{20}H_{33}NO_3$ | 71.60 | 9.92 | 4.18 |

EXAMPLE 10

2.5 Parts of methyl 5-(2,4-dihydroxyphenyl)-5-methylhexanoate and 5.0 parts of n-octylamine are sealed into a glass Carius tube for 3 days at 120° C. The cooled reaction mixture is taken up in ether, washed first with dilute hydrochloric acid until free of the excess oxtylamine, and then with water. After removing the ether, the residual oil, on dilution with 40°–60° C. petroleum ether containing a little ether yields 5-(2,4-dihydroxyphenyl)-5-methylhexanoic acid-n-octylamide m.p. 110°–113° C. with the following percentage composition by weight.

|  | Carbon | Hydrogen | Nitrogen |
|---|---|---|---|
| Found | 71.99 | 9.99 | 3.90 |
| Calculated for $C_{21}H_{35}NO_3$ | 72.17 | 10.09 | 4.01 |

The following compounds are prepared similarly:

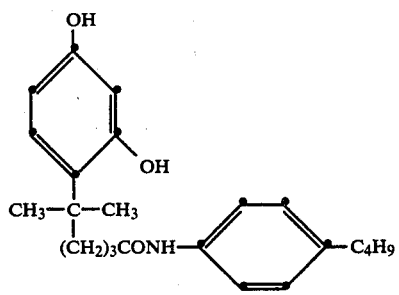
(101)

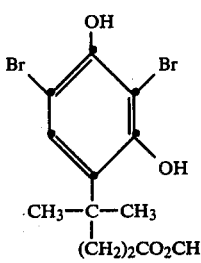
(102)

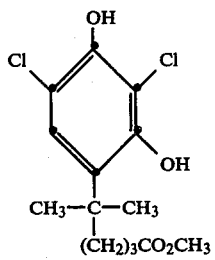
(103)

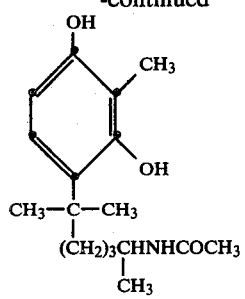
(104)

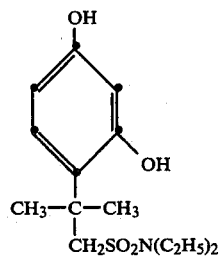
(105)

EXAMPLE 11

5.0 parts of methyl 5-(2,4-dihydroxyphenyl)-5-methylhexanoate, 50 parts of 2-ethyl-hexanol and 0.5 parts of p-toluene sulphonic acid are heated on a steam-bath for 18 hours. The reaction mixture is then diluted with ether, washed with sodium bicarbonate solution, water, and evaporated. The residue, after stripping off excess 2-ethylhexanol on a rotary evaporator at 100° C. and 0.13 mb pressure gives 2-ethylhexyl 5-(2,4-dihydroxyphenyl)-5-methylhexanoate as a viscous amber liquid with the following percentage composition by weight.

|  | Carbon | Hydrogen |
|---|---|---|
| Found | 71.94 | 9.89 |
| Calculated for $C_{21}H_{34}O_4$ | 71.96 | 9.78 |

EXAMPLE 12

Similarly prepared according to the procedure of Example 11 using n-dodecanol in place of 2-ethylhexanol, n-dodecyl 5-(2,4-dihydroxyphenyl)-5-methyl-hexanoate. This obtained as a amber syrup with the following percentages composition by weight.

|  | Carbon | Hydrogen |
|---|---|---|
| Found | 74.24 | 10.38 |
| Calculated for $C_{25}H_{42}O_4$ | 73.85 | 10.41 |

EXAMPLE 13

55.0 parts of resorcinol, 17.8 parts of dimethyl prenyl-phosphonate and 5.0 parts of Fulmont 23 (trademark) are stirred at 125° C. for 18 hours. The cooled reaction mixture is then diluted with ether, filtered free of catalyst, and poured into 500 parts of water. The oil which separated out is then washed by decantation with water and extracted with ether. Following further washes with sodium bicarbonate solution and water, the ether solution after concentration yields dimethyl 3-(2,4-dihydroxyphenyl)-3-methyl-butane-phosphonate, m.p.

142°-3° C., with the following percentage composition by weight.

|  | Carbon | Hydrogen | Phosphorus |
|---|---|---|---|
| Found | 53.97 | 7.33 | 10.94 |
| Calculated for $C_{13}H_{21}O_5P$ | 54.16 | 7.34 | 10.75 |

EXAMPLE 14

Formulation of a resorcinol compound as an oil dispersion

A. 1 g of the resorcinol compound according to Example 1 is dissolved in 1 g isopropylated phenyl phosphate and 1 g ethyl acetate mixture, by heating under reflux; cool to 50° C.

B. 1 ml 10% (v/v in water) sulphonated PEO wetting agent and 3 ml distilled water are added to 8 g 10% (w/w in water, pH 6.5) deionised gelatin at about 50° C.

A and B are then mixed with hand stirring and are dispersed on an ultrasonic mixer for about 30 seconds.

Formulation for coating 0.45 g of the above coupler dispersion are added to 1.70 g 10% deionised gel solution and 0.54 g of a 9.2% iodide silver iodobromide emulsion.

The emulsion contains 162 g silver and 100 g gel in 1467 g total weight. Triazine hardener is added to the formulation at 20 mole/$10^5$ g gel. After adequate mixing, the coating formulation is spread by hand on to 2.4 $dm^2$ polyester base, maintained at 40° C. during coating. Coupler and silver coating weights are approximately 25 mg/$dm^2$ with a gel coating weight of about 80 mg/$dm^2$. Coating are dried and then incubated for about 12 hours at 45° C., 65% R.H. The coatings are overall exposed to white light for 10 seconds and processed as follows at 38° C.

| Development 5 minutes | 0.37 g | $K_2CO_3$ |
|---|---|---|
|  | 1.5 ml | $K_2SO_3$, 65% solution |
|  | 1.05 g | KBr |
|  | 6.0 ml | DTPA (35% solution) |
|  | 2 g | Hydroxylamine sulphate |
|  | 1 ml | $H_2SO_4$ (5N) |
|  | 2.40 g | $CD_4$ |
|  | 1.33 g | $Na_2S_2O_5$ |
|  | 0.94 ml | Acetic acid (80% w/v) |
|  | $H_2O$ to 1 liter pH 10.20 |  |
| Bleach 6¼ minutes | Ammonium bromide | 150 g |
|  | Ferric ammonium EDTA | 112 g |
|  | EDTA | 2.5 g |
|  | Sodium nitrate | 35 g |
|  | Acetic acid, glacial | 10 ml |
|  | Water to | 1 liter |
|  | pH 6.0 ± 0.2 |  |
| Fix. 6¼ minutes | Ammonium thiosulphate | 130 g |
|  | Disodium EDTA | 1.25 g |
|  | Sodium metabisulphite | 12 g |
|  | pH 6.5 ± 0.2 |  |
| Wash 3 minutes (38° C.). | | |

$CD_4$ is 4-[N—ethyl-N—(2'-hydroxyethyl)-amino]-2-methylaniline-hydrosulphate
EDTA is Ethylenediamine tetra-acetic acid
DTPA is Diethylenetriamine penta-acetic acid.

The attached adsorption spectrum shows that a very black dye is obtained which absorbs very well over the entire visible spectrum.

EXAMPLE 15

Coatings were prepared as in example 14 but using the compound prepared in Example 8 above. After processing as in example 14 a grey dye coating was produced, having absorption with broad λmax at about 500 nm and about 600 nm.

EXAMPLE 16

A coating was prepared as in example 14 but using the compound of formula 104. After processing as in example 14 a dye coating is produced with broad absorption having λmax of around 580-590 nm.

What is claimed is:

1. A photographic silver halide material which comprises at least one silver halide emulsion layer coated on a support, there being present in the silver halide emulsion layer(s), or in a layer in operative contact with at least one silver halide emulsion layer, a compound of the formula

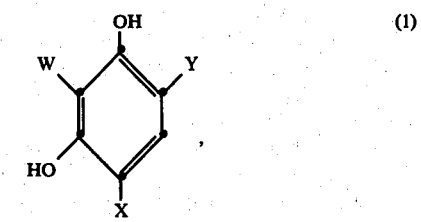

(1)

wherein
W is hydrogen, n-alkyl having 1 to 5 carbon atoms, —NHCOR[1] or —COR[1], wherein R[1] is alkyl having 1 to 12 carbon atoms or alkenyl having 2 to 12 carbon atoms, cycloalkyl having 3 to 8 carbon atoms, aralkyl having 7 to 13 carbon atoms or aryl having 6 to 10 carbon atoms optionally substituted by one or two alkyl groups each having 1 to 4 carbon atoms, a phenoxymethylamino group optionally substituted with one or more alkyl groups, or halogen;

X is hydrogen, chlorine, bromine, a group of formula —SR[11], wherein R[11] is alkyl having 1 to 20 carbon atoms, aryl having 6 to 10 carbon atoms optionally substituted by one or two alkyl groups each having 1 to 4 carbon atoms, or a heterocyclic group, or X is a nitrogen-containing heterocyclic residue attached at a ring nitrogen atom;

Y is a group having the formula

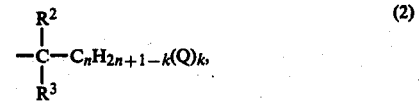

(2)

wherein Q is selected from the residues:
(a) —$COOR^4$ or —$CONR^4R^5$, where $R^4$ is hydrogen, alkyl having 1 to 20 carbon atoms optionally interrupted by 1 or more oxygen atoms, alkenyl having 3 to 20 carbon atoms, cycloalkyl having 3 to 12 carbon atoms, aralkyl having 7 to 13 carbon atoms or optionally substituted aryl having 6 to 10 carbon atoms and $R^5$ is hydrogen or alkyl having 1 to 20 carbon atoms or $R^4$ and $R^5$, together with the nitrogen atom to which they are each bonded, form a 5- or 6-membered heterocyclic ring optionally substituted by alkyl having 1 to 4 carbon atoms, (b) —OM wherein M is $R^5$ or —$COR^6$ wherein $R^5$ is as defined above and $R^6$ is hydrogen, alkyl having 1 to 20 carbon atoms, alkenyl having 3 to 20 carbon atoms, cycloalkyl having 3 to 12 carbon atoms, aralkyl having 7 to 13 carbon atoms or optionally substituted aryl having 6 to 10 carbon atoms, (c) —NR$^7$R$^8$ wherein R$^7$ is hydrogen or alkyl having 1 to 4 carbon atoms and R$^8$ is hydrogen, alkyl having 1 to 4 carbon atoms or acyl of the formula —COR$^4$, wherein R$^4$ is as defined above or R$^7$ and R$^8$, together with the nitrogen atom to which they are bonded, form a 5- or 6-membered heterocyclic ring optionally substituted by alkyl having 1 to 4 carbon atoms, (d) —P(O)(OR$^9$)(O)$_x$R$^{10}$ wherein x is 0 or 1, R$^9$ is hydrogen or alkyl having 1 to 20 carbon atoms, R$^{10}$ is hydrogen or alkyl having 1 to 20 carbon atoms if x is 1, and R$^{10}$ is alkyl containing 1 to 5 carbon atoms if x is 0 or R$^9$ and R$^{10}$ may be linked together fo form an alkylene chain having 2 or 3 carbon atoms optionally substituted by one or more alkyl groups each having 1 to 20 carbon atoms, (e) —SO$_2$T where T is —OH or —NR$^4$R$^5$ wherein R$^4$ and R$^5$ are as defined above and (f) —CN, n is an integer from 1 to 20; k is 1 or 2; R$^2$ and R$^3$ independently are alkyl having 1 to 5 carbon atoms and, if Q is —CO$_2$R$^4$, either R$^2$ or R$^3$ is optionally substituted by one or two —CO$_2$R$^4$ groups, or at least one of R$^2$ and R$^3$ is so linked to the residue —C$_n$H$_{2n+1-k}$— that there is formed a cycloalkylene residue having 5 to 12 carbon atoms substituted by —(CO$_2$R$^4$)$_k$ in which the groups R$^4$ are the same or different and wherein R$^4$ and k are as defined above, or salts thereof with acids or bases.

2. Material according to claim 1, wherein

W is hydrogen, n-alkyl having 1 to 5 carbon atoms, cyclopentyl, cyclohexyl, phenyl optionally substituted by one or two alkyl groups each having 1 to 4 carbon atoms or W is halogen, X is hydrogen, chlorine, bromine, —SR$^{11}$ where R$^{11}$ is alkyl having 1 to 10 carbon atoms, phenyl optionally substituted by one or two alkyl groups each having 1 to 4 carbon atoms or a tetrazolyl ring optionally substituted by alkyl having 1 to 4 carbon atoms or phenyl, Y is a group of the formula

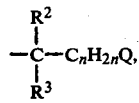

where Q is —COOR$^4$ or —CONR$^4$R$^5$ where R$^4$ is hydrogen, alkyl having 1 to 12 carbon atoms optionally interrupted by 1 or 2 oxygen atoms, benzyl or phenyl and R$^5$ is hydrogen or alkyl having 1 to 10 carbon atoms, or R$^4$ and R$^5$, together with the nitrogen atom to which they are bonded form a morpholinyl or a piperidinyl radical, or Q is —OM, where M is hydrogen or alkyl having 1 to 5 carbon atoms, or M is —COR$^6$ where R$^6$ is hydrogen, alkyl having 1 to 10 carbon atoms, cyclohexyl, phenyl or benzyl, or Q is —NR$^7$R$^8$ where R$^7$ is hydrogen or alkyl having 1 to 4 carbon atoms and R$^8$ is —COR$_4$ where R$_4$ is as defined above, or Q is —P(O)-(OR$^9$)$_2$ where R$^9$ is alkyl having 1 to 10 carbon atoms, or Q is —SO$_2$T where T is hydroxy or —NR$^4$R$^5$ where R$^4$ and R$^5$ are as defined above, R$^2$ and R$^3$ are alkyl having 1 to 5 carbon atoms or at least one of R$^2$ and R$^3$ is so linked to the residue —C$_n$H$_{2n}$— that there is formed a cycloalkyl group having 5 to 8 carbon atoms optionally substituted by a group —COOR$^4$ where R$^4$ is as defined above, and n is an integer from 1 to 20.

3. Material according to claim 2, wherein W is hydrogen, methyl, chlorine or bromine, X is hydrogen, chlorine, bromine or a group of the formula

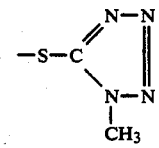

and Y is a group of the formula

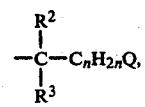

wherein Y is —COOR$^4$ or —CONR$^4$R$^5$, where R$^4$ is hydrogen or alkyl having 1 to 12 carbon atoms and R$^5$ is alkyl having 5 to 10 carbon atoms or phenyl optionally substituted by alkyl having 1 to 4 carbon atoms, or Q is —OM, where M is hydrogen or —COR$_6$ where R$_6$ is alkyl having 1 to 5 carbon atoms, or Q is —NHR$_8$ where R$_8$ is —COR$_6$ where R$_6$ is as just defined or Q is —P(O)(OR$_9$)$_2$, where R$_9$ is alkyl having 1 to 5 carbon atoms, or Q is —SO$_2$NR$^6$R$^6$ where R$^6$ is as defined above and R$_2$ and R$_3$ are alkyl having 1 to 5 carbon atoms or R$_2$ forms together with the residue —C$_n$H$_{2n}$— a cyclohexyl group substituted by —COOR$^4$ where R$^4$ is as defined above, and n is an integer from 1 to 10.

4. Material according to claim 1 wherein R$^2$ is methyl.

5. Material according to claim 1, wherein W is hydrogen, methyl, ethyl, butyl, —NHCOR$^1$ or —COR$^1$ wherein R$^1$ is alkyl having 1 to 6 carbon atoms or alkenyl having 2 to 6 carbon atoms, cyclohexyl, benzyl, phenyl optionally substituted by one or two methyl or ethyl groups, phenoxymethylamino optionally substituted with one or more alkyl groups, or W is chlorine or bromine.

6. Material according to claim 5 wherein W is hydrogen, methyl, —NHCOCH$_2$C$_6$H$_5$, —COCH$_3$, —COC$_6$H$_5$, phenoxymethylamino optionally substituted with one or more alkyl groups, chlorine or bromine.

7. Material according to claim 1 or 2 wherein n is 1 to 10, k is 1, R$^3$ is alkyl having 1 to 5 carbon atoms, Q is —CO$_2$R$^4$ or —CONR$^4$R$^5$ or —NR$^7$R$^8$ wherein R$^4$, R$^5$, R$^7$ and R$^8$ are as defined in claim 1 and W is defined as in claim 6.

8. Material according to claim 7 wherein W is hydrogen, methyl, —NHCOCH$_2$C$_6$H$_5$, —NHCOC$_6$H$_5$ or phenoxymethylamino optionally substituted with one or more alkyl groups, n is 3 to 5, k is 1, R is methyl and Q is —COOR$^4$ or —CONR$^4$R$^5$ or —NR$^7$R$^8$, wherein R$^4$, R$^5$, R$^7$ and R$^8$ are as defined in claim 1.

9. A process for the production of a photographic black dye image which comprises exposing imagewise the photographic material according to claim 1, colour developing the material so exposed using a colour developing solution which comprises an aqueous alkaline solution of a primary aromatic amine colour developing agent, to form simultaneously a silver image and a black dye image, optionally bleaching the silver image, and then fixing out all the silver halide in the material using an aqueous solution of a silver halide solvent.

10. A process according to claim 9 wherein the silver bleach step is combined with the fixing step by employing a bleach-fix bath.

11. A process according to claim 9 wherein the primary aromatic amine colour developing agent is a p-phenylenediamine compound or a p-aminophenol compound.

12. A process according to claim 9 wherein the compound of the formula (1) is incorporated into the silver halide emulsion in an oil dispersion.

13. Processed silver halide photographic material which comprises a photographic black dye image which has been produced by the process according to claim 9.

* * * * *